United States Patent [19]

Sandor et al.

[11] 4,164,141

[45] Aug. 14, 1979

[54] BRINELL TESTING APPARATUS

[75] Inventors: Louis Sandor, Hammond, Ind.; Albert T. Wendt, Keokuk, Iowa

[73] Assignee: AMSTED Industries Incorporated, Chicago, Ill.

[21] Appl. No.: 921,556

[22] Filed: Jul. 3, 1978

[51] Int. Cl.[2] .................................................. G01N 3/48
[52] U.S. Cl. ..................................................... 73/81
[58] Field of Search ..................... 73/81, 82, 83, 78, 85

[56] References Cited

U.S. PATENT DOCUMENTS 3,926,041  12/1975  Shaw ........................................... 73/85

Primary Examiner—Jerry W. Myracle
Attorney, Agent, or Firm—Edward J. Brosius; Fred P. Kostka; John L. Schmitt

[57] ABSTRACT

An improved apparatus for determining the Brinell hardness of railway vehicle wheels comprising a receiving means to accept and retain the wheel in a substantially vertical position; an elevator to raise and lower the receiving means in a substantially vertical plane; a polishing attachment to polish at least a portion of the wheel being held by the receiving means; and a Brinell testing device to determine the hardness of the wheel at one or more points which have previously been polished by the polishing attachment.

10 Claims, 4 Drawing Figures

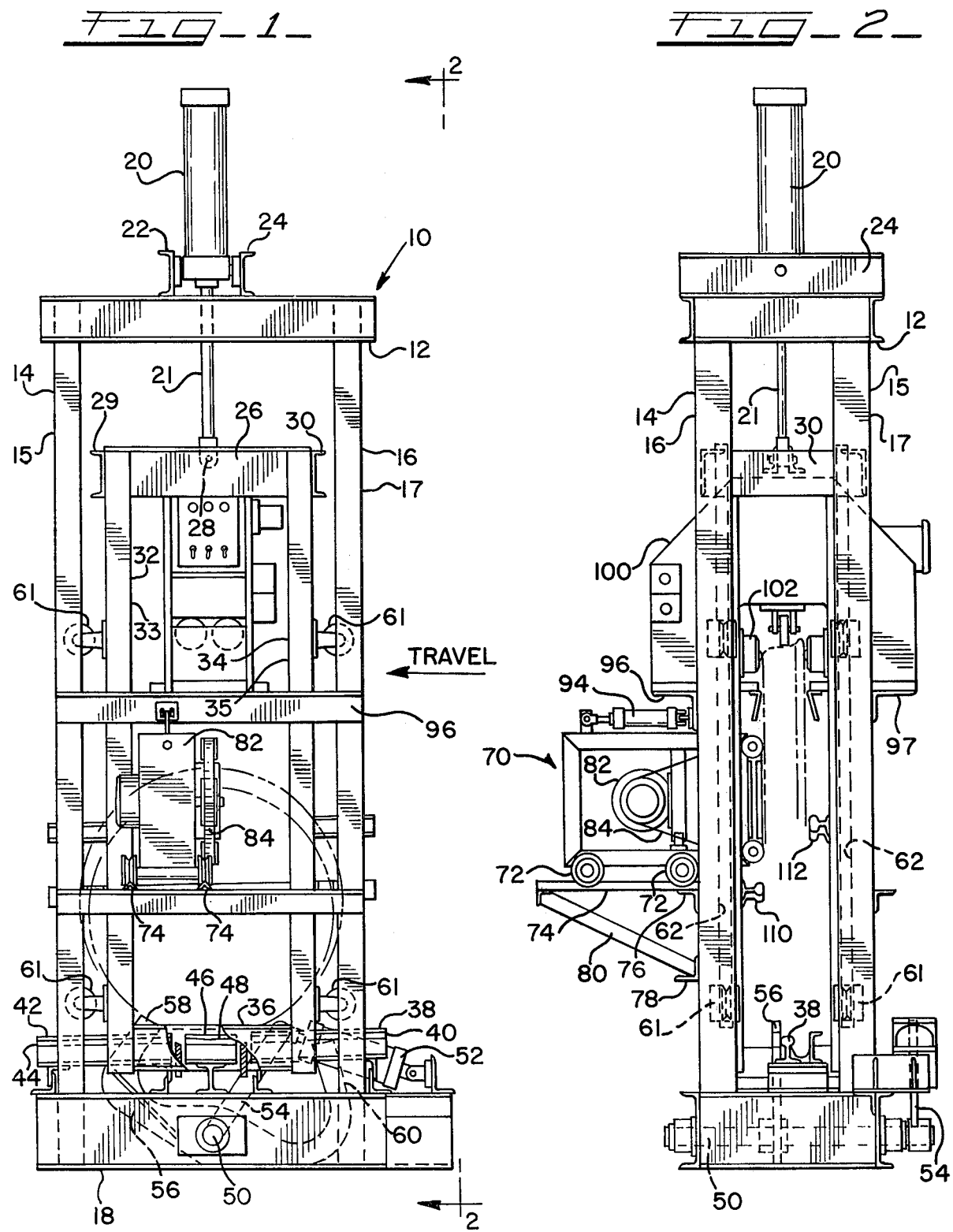

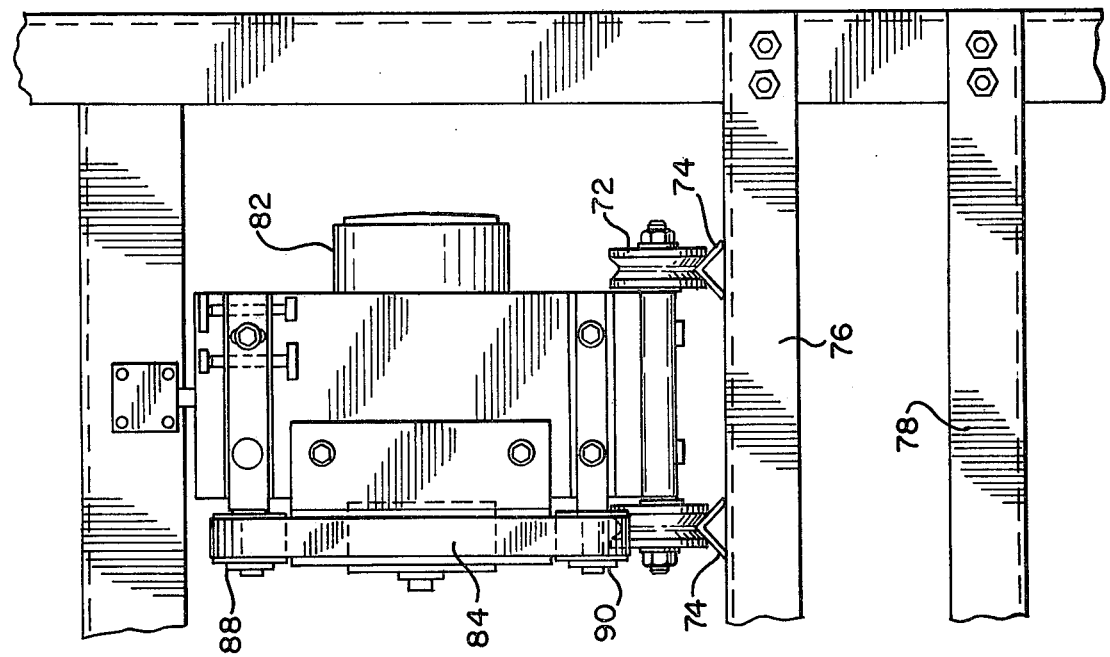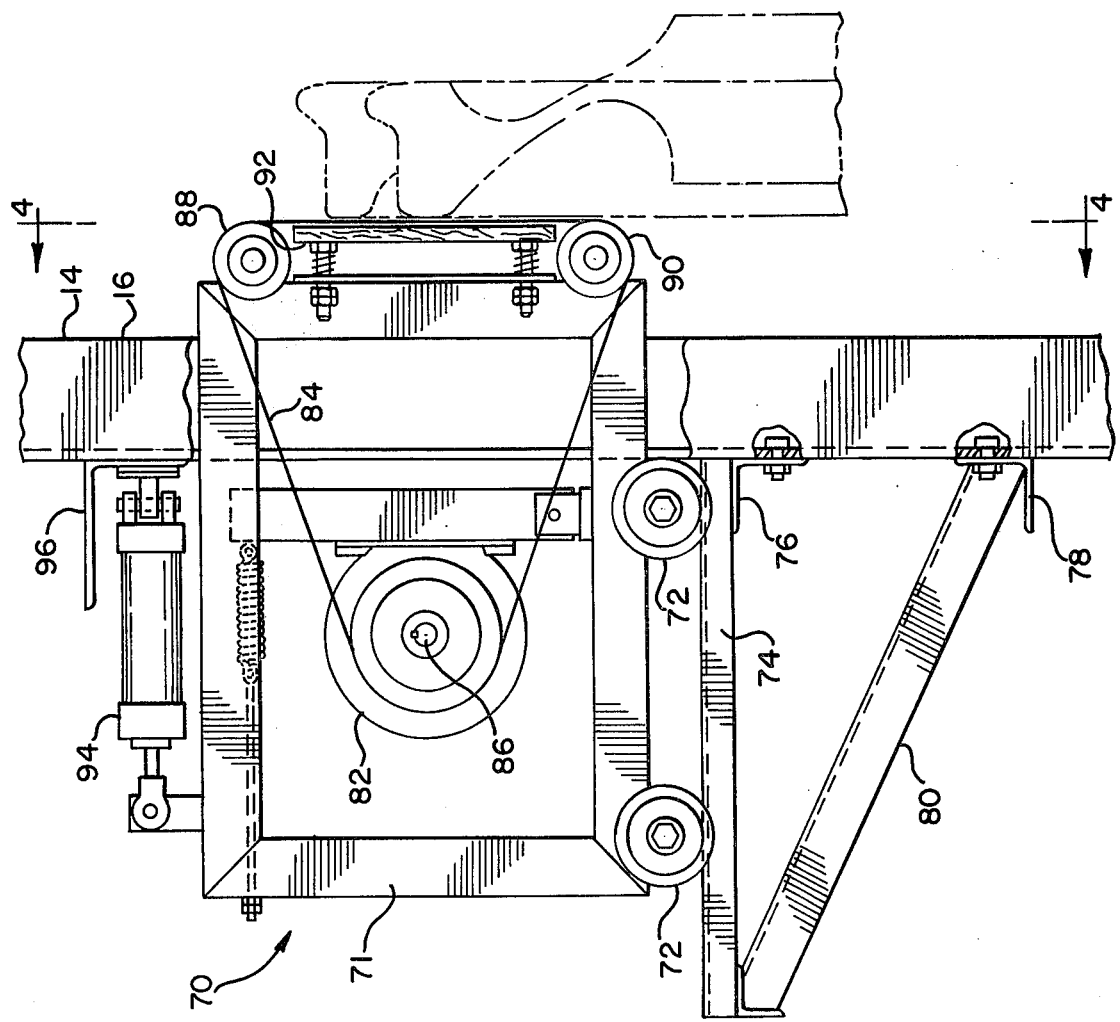

BRINELL TESTING APPARATUS

BACKGROUND AND SUMMARY OF THE INVENTION

This invention relates to an improved apparatus for determining Brinell hardness. More particularly, the invention relates to an improved apparatus for determining the Brinell hardness of railway vehicle wheels.

Brinell ratings are used extensively throughout industry as a measure of material hardness. One such use involves the testing of railway car and locomotive wheels. Because many separate wheels require testing, an efficient and reliable apparatus is desirable. In many instances the surface of the wheels needs to be polished in order to determine accurate hardness ratings. In the past, the various operations involved in Brinell testing of such wheels have resulted in excessive and time consuming movements of the wheel, for example, performing certain operations with the wheel in a horizontal position and other operations with the wheel in a vertical orientation. Clearly, an improved Brinell hardness apparatus for testing railway vehicle wheels would be advantageous.

An improved apparatus for determining the Brinell hardness of railway locomotive and car wheels has now been discovered. The present apparatus comprises a wheel receiving means which acts to receive and retain a railway vehicle wheel in a substantially vertical position during the testing operations.

In any event, the present apparatus further includes an elevator means, preferably powered by an air or hydraulic cylinder-piston assembly, which is positioned with respect to the receiving means so as to raise or lower the receiving means, preferably in a substantially vertical plane, as desired. Thus, when the receiving means is retaining a wheel in the substantially vertical position, the elevator raises or lowers this wheel, preferably straight up or down, as desired.

A polishing mechanism is included in the present apparatus. In order to obtain accurate and reliable Brinell hardness ratings, that portion of the wheel's surface which is to be tested should be thoroughly cleaned or polished so as to expose the base metal. Before the Brinell hardness determinations are made the polishing mechanism is located adjacent the travel path of the elevator in such a position as to polish at least a portion of the surface of the wheel being retained by the receiving means as the wheel is moved in a substantially vertical plane by the elevator.

In a preferred embodiment of the present invention, the polishing mechanism comprises a belt grinder in which the belt travels in a substantially downward direction as the belt contacts the wheel being moved by the elevator. In a further preferred embodiment, the polishing belt grinder, includes a variable pressure system, preferably a hydraulic or air cylinder-piston assembly, in communication with the grinding belt, acting to provide effective contact of the polishing element with the passing wheel so as to polish at least a portion of the wheel.

The present apparatus furthermore includes a Brinell testing system located adjacent to the travel path of the elevator so as to determine the Brinell hardness of that wheel being retained in a substantially vertical position by the receiving means. The Brinell hardness determinations are made on the portion or portions of the surface of the wheel previously polished by the polishing mechanism. Any suitable type of Brinell testing system may be employed in the present apparatus. The conventional "piston-type" Brinell testing system, commonly used to measure the hardness of railway vehicle wheels, is a preferred system.

In another embodiment, the Brinell testing system is located above the polishing element. In this embodiment, the wheel being retained by the receiving means is raised by the elevator past the polishing mechanism and then to the Brinell testing system. Preferably, the wheel comes to a stop, at least momentarily, while the Brinell hardness determinations are being made. After the determination is made, the wheel is lowered away from the Brinell testing system. The wheel is maintained in a substantially vertical position throughout the cycle just described.

In another embodiment, the present apparatus comprises a release mechansim, preferably located near the lower terminous of travel of the elevator. This release mechanism acts to dislodge the wheel from the receiving means after the Brinell determinations have been made. Preferably, the elevator lowers the wheel from the Brinell testing system down to substantially the level at which the wheel was first accepted by the receiving means. At this point, the release mechanism acts to dislodge the already tested wheel from the receiving means. After this wheel has been removed, the receiving means is again ready to accept another wheel for testing. This cycle may be repeated as often as required.

These and other aspects and advantages of the present invention are set forth in the following detailed description and claims, particularly when considered in conjunction with the accompanying drawings in which like parts bear like reference numerals.

BRIEF DESCRIPTION OF THE DRAWINGS

FIG. 1 is a front elevational view of one embodiment of the apparatus of the present invention.

FIG. 2 is a side elevational view taken along line 2—2 in FIG. 1, of the embodiment shown in FIG. 1.

FIG. 3 is an enlarged side elevational view of one portion of the apparatus as shown in FIG. 2.

FIG. 4 is a front elevational view, taken along line 4—4 of FIG. 3, of that portion of the apparatus shown in FIG. 3.

DESCRIPTION OF THE PREFERRED EMBODIMENTS

Referring now to the drawings, the embodiment of the apparatus illustrated is shown generally at 10, and comprises a top frame 12, side legs 14, 15 and 16, 17 and base frame 18 which cooperate to support, directly or indirectly, the other components of the apparatus 10. Air cylinder-piston device 20 is supported on top frame 12 by supports 22 and 24. Piston rod 21 of air cylinder-piston device 20, is secured to top beam 26 by bolt 28. Top bars 29 and 30 depend from top beam 26 and act to hold side bars 32, 33 and 34, 35 affixed to top beam 26. Side bars 32, 33 and 34, 35 terminate on base 36. Top beam 26, top bars 29 and 30, side bars 32, 33 and 34, 35, and base 36 move together in response to the action of air cylinder-piston device 20 through piston rod 21.

Base 36 includes or supports entrance rail 38, entrance guide 40 and exit rail 42 and exit guide 44 which act to provide for efficient access to and egress from the apparatus 10 for railway vehicle wheels. Access to and egress from the apparatus 10 is accomplished by using entrance and exit rails 38 and 42 and entrance and exit guides 40 and 44 with the wheel being in a substantially vertical position. In approximately the central portion of the base 36, central rail 46 and central guide 48 are located and act to retain the railway vehicle wheel in the apparatus 10 for Brinell hardness determination. As shown in FIG. 1, central guide 48 has slightly sloping side walls which aid in retaining the wheel in apparatus 10 and act to insure that any diameter wheel is centered in the apparatus 10.

Shaft 50 is located in proximity to base frame 18. Shaft 50 rotates in response to the action of cylinder-piston device 52, which is attached to base frame 18. Cylinder-piston device 52 acts directly to move one end of connector 54 while the other end of connector 54 is affixed to shaft 50. Thus, as connector 54 moves in response to cylinder-piston device 52, shaft 50 is caused to rotate.

U-shaped element 56 is attached to shaft 50 in such a manner as to rotate with shaft 50. U-shaped element 56 is positioned so that each of the legs 58 and 60 of U-shaped element 56 comes into contact with the railroad vehicle wheel being tested during certain portions of the testing cycle, as described hereinafter.

The up and down movement of top beam 26, top bars 29 and 30, side bars 32, 33 and 34, 35 and base 36 in response to the action of air cylinder-piston device 20 is guided or stabilized by a series of rollers 61 attached to each of the side bars 32, 33 and 34, 35. Rollers 61 are made to run in grooves 62 in each of the stationary side legs 14, 15 and 16, 17. In this manner, the up and down movement of the top beam 26, top bars 29 and 30, side bars 32, 33 and 34, 35 and base 36 is controlled with respect to stationary top frame 12, side legs 14, 15 and 16, 17 and base frame 18, which support the other components of apparatus 10. This control of the up and down movement aids in insuring proper cooperation of the various components of apparatus 10.

The polishing attachment, shown generally at 70, includes housing 71 which sits on four wheels 72 which, in turn are made to move along rails 74. The rails 74 are affixed to stationary side legs 14 and 16 with angle supports 76 and 78 and bare supports 80. Polishing attachment 70 further includes motor 82 which acts to drive grinding belt 84 in a generally clockwise direction, as shown in FIG. 3, around shaft 86, and rollers 88 and 90. Stationary backing 92, bolted to housing 71, provides support for grinding belt 84, driving that portion of the cycle in which the grinding belt 84 comes in contact with the railway vehicle wheel.

A cylinder-piston device 94 has one end affixed to stationary side legs 14 and 16 by angle support 96 and the other end attached to housing 71. The action of cylinder-piston device 94 causes polishing attachment 70 to move, on wheels 72 over rails 74, in and out of the travel path of the railway vehicle wheel as the wheel moves up and down in apparatus 10. Such in and out movement of polishing attachment 70 insures sufficient contact of the grinding belt 84 with the wheel to properly polish the surface of the wheel for determining Brinell hardness.

A conventional piston-type Brinell testing device 100 is supported in a stationary position on angle supports 96 and 97. Brinell testing device 100 is positioned above grinding attachment 70, with respect to the up and down travel path of the railway vehicle wheel in apparatus 10. Brinell testing device 100 functions in a conventional manner through piston 102 and the other standard components of Brinell testing device 100, to determine the Brinell hardness of the wheel at a point or points on the wheel which have been properly prepared, e.g., polished, by the action of polishing attachment 70. Preferably, the wheel is stopped, at least momentarily, in its up and down cycle while the Brinell hardness determinations are being made.

Throughout the functioning of apparatus 10 the railway vehicle wheel being tested is maintained in a substantially vertical position. Guide rails 110 and 112, attached to side bars 32 and 34 and side bars 33 and 35 respectively, to aid in insuring that the wheel remains in a substantially vertical position.

Apparatus 10 functions as follows: With base 36 in its lowermost position, a railway vehicle wheel to be tested is caused to roll in a substantially vertical position on entrance rail 38 and entrance guide 40. The substantially vertical wheel is cradled in the slightly sloping walls of central guide 48. Also, at this point in the cycle, leg 58 of U-shaped element 56 is positioned, by the action of cylinder-piston device 52 on shaft 50, as shown in FIG. 1, so as to prevent the wheel from exiting the apparatus 10, and to aid in centering the substantially vertical wheel.

Once the wheel is in place, a cylinder-piston device 20 is actuated, causing top beam 26, top bars 29 and 30, side bars, 32, 33 and 34, 35 and base 36, together with the substantially vertical wheel, to move upward. As the wheel moves past the polishing attachment 70, grinding belt 84 comes in contact with a portion of the surface of the wheel to properly polish that portion of the wheel for Brinell testing. Cylinder-piston device 94 is activated and functions, as described previously, to provide the proper degree of contacting between the downwardly rotating grinding belt 84 and the upwardly moving wheel to provide proper wheel surface preparation.

As the wheel continues to move upward, that portion of the wheel which has been prepared by the polishing attachment 70, enters the throat of Brinell testing device 100. The properly prepared surface comes in contact with the Brinell piston 102 and one or more Brinell hardness determinations are made. During such testing the wheel remains in a substantially vertical position.

After the Brinell determinations have been made, the wheel is caused to be lowered to the position which it occupied when it first entered the apparatus 10. At this point cylinder-piston device 52 is activated and causes U-shaped element to move so that leg 58 moves away from the wheel and leg 60 to move into contact with the wheel. The contact of leg 60 with the already tested wheel acts to dislodge or release the wheel from the central rail 46 and central guide 48 and cause the wheel to exit the apparatus 10 via exit rail 42 and exit guide 44. Cylinder-piston device 52 is again activated to cause the U-shaped element 56 to return to its original position, as shown in FIG. 1. Apparatus 10 is ready for the operation cycle, described above, to be repeated.

The present apparatus provides for quick, efficient and reliable Brinell hardness determinations for railway vehicle wheels. Throughout the testing cycle the wheel remains in substantially vertical position which results in significant reduction in the number of time consuming motions required to perform such tests.

While this invention has been described with respect to various specific examples and embodiments, it is to be understood that the invention is not limited thereto, and that it can be variously practiced within the scope of the following claims.

What is claimed is:

1. An improved apparatus for determining the Brinell hardness of railway vehicle wheels comprising receiving means acting to accept and retain said wheel in a substantially vertical plane; elevator means positioned with respect to said receiving means so as to raise or lower said receiving means in a substantially vertical plane as desired; polishing means located in proximity to the travel path of said elevator means so as to polish at least a portion of said wheel being retained by said receiving means as said wheel is moved in a substantially vertical plane by said elevator means; and Brinell testing means located in proximity to the travel path of said elevator means so as to determine the Brinell hardness of said wheel at one or more points on said wheel polished by said polishing means.

2. The apparatus of claim 1 wherein said testing means is located above said polishing means.

3. The apparatus of claim 1 wherein said testing means is substantially stationary relative to the travel path of said elevator means.

4. The apparatus of claim 1 which further comprises release means acting to dislodge said wheel from said receiving means after said Brinell hardness is determined.

5. The apparatus of claim 4 wherein said release means is located near the lower end of the travel path of said elevator means.

6. The apparatus of claim 4 wherein said release means acts to dislodge said wheel from said receiving means, after said elevator means lowers said wheel to substantially the same level at which said receiving means first accepted said wheel.

7. The apparatus of claim 1 wherein said polishing means comprises a belt grinder.

8. The apparatus of claim 7 wherein said grinding belt travels in a substantially downward direction as said belt contacts said wheel.

9. The apparatus of claim 7 wherein said belt grinder includes variable pressure means in communication with said grinding belt acting to provide effective contact of said grinding belt with said passing wheel so as to polish at least a portion of said wheel.

10. The apparatus of claim 1 wherein said receiving means includes sloped guide rails forming a generally V-shaped trough into which said wheel is positioned during testing.

* * * * *